(12) United States Patent
Tang

(10) Patent No.: US 10,372,875 B2
(45) Date of Patent: Aug. 6, 2019

(54) METHOD AND APPARATUS FOR TRACKING CONTEXT SYNCHRONIZATION ACROSS MULTIPLE APPLICATIONS

(71) Applicant: Change Healthcare Holdings, LLC, Nashville, TN (US)

(72) Inventor: Xiaowei Tang, Richmond (CA)

(73) Assignee: CHANGE HEALTHCARE HOLDINGS, LLC, Nashville, TN (US)

( * ) Notice: Subject to any disclaimer, the term of this patent is extended or adjusted under 35 U.S.C. 154(b) by 808 days.

(21) Appl. No.: 15/076,071

(22) Filed: Mar. 21, 2016

(65) Prior Publication Data

US 2017/0270247 A1    Sep. 21, 2017

(51) Int. Cl.
*G06F 19/00* (2018.01)
*G06F 9/54* (2006.01)
*G06F 17/30* (2006.01)
*G06F 16/51* (2019.01)

(52) U.S. Cl.
CPC ............ *G06F 19/321* (2013.01); *G06F 9/542* (2013.01); *G06F 16/51* (2019.01)

(58) Field of Classification Search
CPC .......... G06Q 10/06; G06Q 10/063114; G06Q 50/24; G16H 40/20; G16H 50/70; G06F 16/51; G06F 19/00; G06F 19/321; G06F 19/328
See application file for complete search history.

(56) References Cited

U.S. PATENT DOCUMENTS

| 2005/0071194 A1* | 3/2005 | Bormann ............... G06Q 50/22 705/2 |
| 2007/0050359 A1* | 3/2007 | Anderson ............. G06F 19/321 |
| 2012/0130734 A1* | 5/2012 | White .................... G06Q 50/22 705/2 |

* cited by examiner

*Primary Examiner* — Maroun P Kanaan
(74) *Attorney, Agent, or Firm* — Alston & Bird LLP

(57) ABSTRACT

A method, computing device and computer program product are provided according to an example embodiment in order to track context synchronization of files operating on a plurality of participating applications. A synchronization tracking tool may receive contexts from a plurality of participating applications and provide an indication of a synchronization state based upon the timing and contexts received from the participating applications. An indication of the synchronization state may be provided to a user via a user interface in a visual and/or audible manner. The participating applications may further request synchronization state information from the synchronization tool.

20 Claims, 6 Drawing Sheets

Example 1:

| Time  | RIS | PACS | Reporting | Synchronization State                      |
|-------|-----|------|-----------|--------------------------------------------|
| 0:00.0| -   | -    | -         | No Context                                 |
| 0:00.5| A   | -    | -         | Context Change Started / Local Context Only|
| 0:01.0| A   | A    | -         | In Progress                                |
| 0:02.0| A   | A    | A         | Synchronized                               |

Example 2:

| Time  | RIS | PACS | Reporting | Synchronization State   |
|-------|-----|------|-----------|-------------------------|
| 0:00.0| A   | A    | A         | Synchronized            |
| 0:01.0| A   | B    | A         | Context Change Started  |
| 0:01.5| -   | B    | A         | In Progress             |
| 0:02.0| -   | B    | -         | In Progress             |
| 0:02.5| B   | B    | -         | In Progress             |
| 0:03.0| B   | B    | B         | Synchronized            |

FIG. 4

Example 3:

| Time | RIS | PACS | Reporting | Synchronization State |
|---|---|---|---|---|
| 0:00.0 | A | A | A | Synchronized |
| 0:01.0 | A | B | A | Context Change Started |
| 0:01.5 | - | B | A | In Progress |
| 0:02.0 | - | B | - | In Progress / Local Context Only |
| 0:02.5 | B | B | - | In Progress |
| 0:03.0 | B | B | C | Out-of-Sync |

Example 4:

| Time | RIS | PACS | Reporting | Synchronization State |
|---|---|---|---|---|
| 0:00.0 | A | A | A | Synchronized |
| 0:01:0 | A | B | A | Context Change Started |
| 0:02:0 | - | B | A | In Progress |
| 0:03.0 | - | B | - | In Progress / Local Context Only |
| 0:04.0 | - | C | - | Context Change Started |
| 0:05.0 | B | C | - | In Progress |
| 0:06.0 | C | C | - | In Progress |
| 0:07.0 | C | C | B | Out-of-Sync |

FIG. 5

METHOD AND APPARATUS FOR TRACKING CONTEXT SYNCHRONIZATION ACROSS MULTIPLE APPLICATIONS

TECHNOLOGICAL FIELD

An example embodiment of the present invention relates generally to synchronizing contexts across multiple applications, and more particularly, to tracking context synchronization across multiple applications while providing alerts indicative of out-of-sync applications and determining the severity of any applications out-of-sync using a time-domain factor.

BACKGROUND

Electronic record keeping, databases, reports, and studies, have become more prevalent with the ubiquity of computers in a variety of environments from retail store operations to healthcare facilities. While these electronic files may be related to one another, some files may require different applications to view, edit, and/or interact with the files. A comprehensive review of information relating to a particular entity may require simultaneous review or interaction with multiple electronic files associated with the entity. However, the multiple electronic files may require different applications to view, edit, and/or interact with the files. Operating these various applications simultaneously while ensuring that the various files are associated with the same entity may be cumbersome and problematic.

BRIEF SUMMARY

A method, computing device and computer program product are provided according to an example embodiment in order to synchronize contexts of files operating on a plurality of participating applications. According to an example embodiment, a radiology information system is provided including a processor, at least one non-transitory memory having program code portions stored thereon, and a radiology information database having radiology images stored therein. The program code portions may be configured to, upon execution: receive an indication of two or more participating applications; receive a first patient context associated with a first file in response to a first application of the two or more applications accessing the first file associated with a first patient stored in the radiology information database; determine if the first patient context is different from patient contexts associated with other applications of the two or more participating applications; initiate a timer in response to determining that the first patient context is different from the patient contexts associated with the other applications; determine if the patient contexts associated with the other applications have changed to become the first patient context; provide a first notification in response to the patient context associated with at least one of the other applications not matching the first patient context and the timer satisfying a first criterion; and provide a second notification in response to the patient context associated with at least one of the other applications not matching the first patient context and the timer satisfying a second criterion.

According to some embodiments, the system may further include program code portions configured to provide a third notification in response to the patient contexts associated with the other applications matching the first patient context. Embodiments may include program code portions configured to map the patient contexts associated with the two or more participating applications to a common patient context format. The first notification may include an in-progress notification indicating a number of the other applications associated with patient contexts not matching the first patient context. The program code portions configured to provide a second notification in response to the patient context associated with at least one of the other applications not matching the first patient context comprises program code portions configured to provide an indication of a number of applications for which a patient context does not match the first patient context.

Embodiments may optionally include program code portions configured to: determine a severity level based on a number of other applications for which a patient context does not match the first patient context and the timer satisfying the first criterion and a number of other applications for which a patient context does not match a first patient context and the timer satisfying the second criterions; and append information associated with one of the first notification or the second notification and the determined severity level to a study associated with the first patient.

Embodiments of the present invention may provide an apparatus including a processor and at least one non-transitory memory having computer-executable program code instructions stored therein. The processor may be configured to, in response to execution of the computer-executable program code instructions, cause the apparatus to: receive an indication of two or more participating applications; receive a first patient context associated with a first file in response to a first application of the two or more applications accessing a file associated with a first patient; determine if the first patient; determine if the first patient context is different from patient contexts associated with other applications of the two or more participating applications; initiate a timer in response to determining that the first patient context is different from the patient contexts associated with the other applications; determine if the patient contexts associated with the other applications have changed to become the first patient context; provide a first notification in response to the patient context associated with at least one of the other applications not matching the first patient context and the timer satisfying a first criterion; and provide a second notification in response to the patient context associated with at least one of the other applications not matching the first patient context and the timer satisfying a second criterion.

According to some embodiments, the file may be a radiology study, and at least one of the two or more applications includes a radiology image viewing application. The apparatus may be configured to map the patient contexts associated with the two or more participating applications to a common patient context format. The first notification may include an in-progress notification indicating a number of the other applications associated with the patient contexts not matching the first patient context. Causing the apparatus to provide a second notification may include causing the apparatus to provide an indication of a number of applications for which a patient context does not match the first patient context.

According to some embodiments, the apparatus may be configured to determine a severity level based on a number of other applications for which a patient context does not match the first patient context and the timer satisfies the first criterion, and a number of other applications for which a patient context does not match the first patient context and the timer satisfies the second criterion. The severity level may be appended to a study associated with the first patient.

The apparatus may be configured to receive an acknowledgement of the first notification or the second notification, where causing the apparatus to determine the severity level may optionally be based on whether an acknowledgment is received for the first notification or the second notification.

Embodiments of the present invention may provide a method including: receiving an indication of two or more participating applications; receiving a first patient context associated with a first file in response to a first application of the two or more applications accessing a file associated with a first patient; determining if the first patient context is different from patient contexts associated with other applications of the two or more participating applications; initiating a timer in response to determining that the first patient context is different from the patient contexts associated with the other applications; determining if the patient contexts associated with the other applications have changed to become the first patient context; providing a first notification in response to the patient context associated with at least one of the other applications not matching the first patient context and the timer satisfying a first criterion; providing a second notification in response to the patient context associated with at least one of the other applications not matching the first patient context and the timer satisfying a second criterion; and appending information associated with one of the first notification or the second notification to a study associated with the first patient.

The method of example embodiments may include mapping the patient contexts associated with the two or more participating applications to a common patient context format. The study may include a radiology study, and at least one of the two or more applications may include a radiology viewing application. The first notification may include an in-progress notification indicating a number of the other applications associated with patient contexts not matching the first patient context. Providing the second notification may include providing an indication of a number of applications for which a patient context does not match the first patient context.

According to some embodiments, methods may include determining a severity level based on a number of the other applications for which a patient context does not match the first patient context and the timer satisfies the first criterion and a number of the other applications for which a patient context does not match the first patient context and the timer satisfies the second criterion. The severity level may be included in the information appended to the study associated with the first patient. Methods may include receiving an acknowledgement of the first notification or the second notification, where determining a severity level may optionally be based on whether an acknowledgement is received for the first notification or the second notification.

BRIEF DESCRIPTION OF THE DRAWINGS

Figure 1:
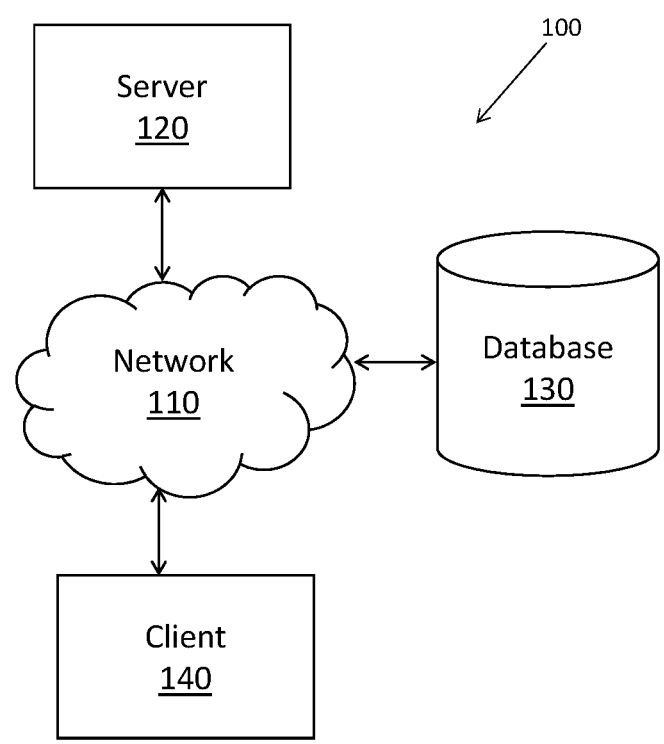
Figure 2:
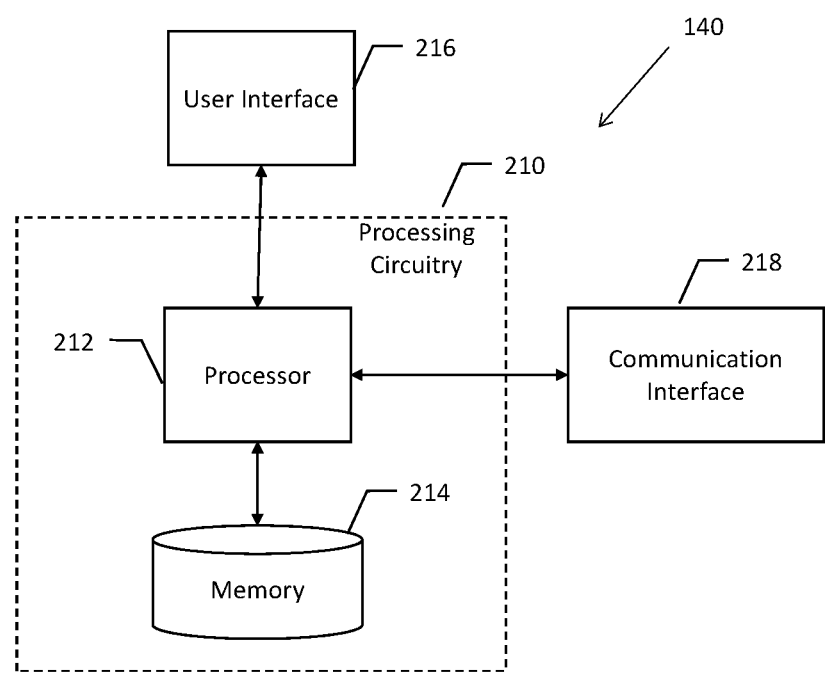
Figure 3:
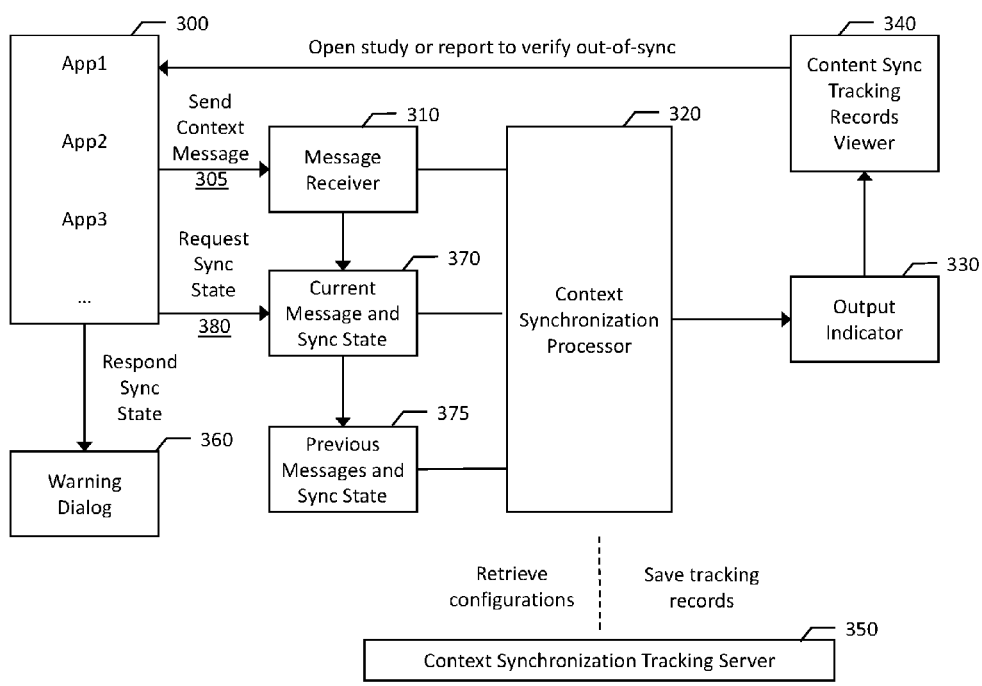
Figure 6:
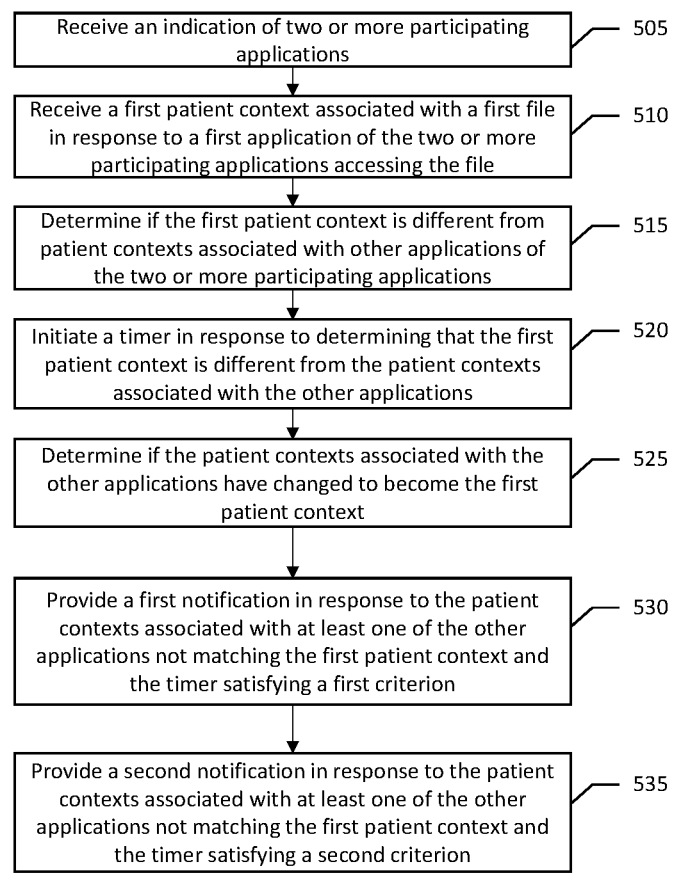

Having thus described certain example embodiments of the invention in general terms, reference will now be made to the accompanying drawings, which are not necessarily drawn to scale, and wherein:

FIG. 1 is a schematic representation of a system for tracking context synchronization across a plurality of participating applications in accordance with an example embodiment of the present invention;

FIG. 2 is a block diagram of a client that may be specifically configured in accordance with an example embodiment of the present invention;

FIG. 3 is a block diagram of the message flow for synchronizing contexts across a plurality of participating applications according to an example embodiment of the present invention;

FIG. 4 illustrates two examples of context synchronization states during a context synchronization cycle according to an example embodiment of the present invention;

FIG. 5 illustrates two more examples of context synchronization states during a context synchronization cycle according to an example embodiment of the present invention; and FIG. 6 is a flowchart of a method of operating a synchronization tool according to example embodiments of the present invention.

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Further, the apparatus and method of example embodiments of the present invention will be primarily described in conjunction with medical-imaging applications. It should be understood, however, that the apparatus and method may be utilized in conjunction with a variety of other applications, both in the medical industry and outside the medical industry. Like numbers refer to like elements throughout.

Electronic record keeping, databases, reports, and studies, may be collected through various means of data collection and data entry to create electronic files representative of various forms of information. Electronic files may include sales records, projections, inventory on-hand, future estimated demand, health records, laboratory reports, health studies, radiology studies, or any number of electronic files generated through the plethora of applications available. In some cases, multiple electronic files may be related to a common subject, and a user may wish to review the plurality of electronic files simultaneously. These electronic files may be associated with differing applications such that the files cannot be opened each within the same application. With the routine advancement of technology and the development of new applications, it is inevitable that some electronic files will not be compatible with other software application types. As such, multiple applications may be required to open multiple electronic files related to the same subject for simultaneous review. While examples embodiments of the present invention may be implemented in a variety of environments, an example embodiment described in detail herein will be focused on a healthcare environment. Specifically, the example embodiment relates to electronic radiological studies and the review thereof. However, this example embodiment is not intended to be limiting as it will be appreciated that example embodiments of the present invention can be implemented in a variety of different environments.

In the healthcare industry, a user, such as a healthcare worker, clinician, physician, technician, nurse, radiologist, etc., routinely uses a computer to view multiple computer applications relating to various patients. The computer may provide easy access to medical records contained in various computer application formats for patients that are conveniently accessed through a computer workstation. A healthcare professional may review various medical records of a patient contained in multiple, disparate computer applications to compare and correlate the data contained in the electronic files associated with the patient. Each application may display different information about a patient or entity. The information contained in disparate applications may be reviewed and aggregated by the user who may be, for example, attempting to diagnose a patient.

Due to the ease with which a user may change between entities (i.e., patients) among the various simultaneously operating applications, the possibility exists that the user may be viewing information in one application for one patient and information in another application for a different patient. If the user does not realize that the information being viewed in the disparate applications are for different patients, the information may be misinterpreted and problems can arise that can affect patient safety.

Accordingly, there is a need to provide an easy and accurate method for determining and indicating context synchronization of disparate applications running on a computer, such as a patient context. Further, embodiments described herein enable applications to periodically determine the context of other participating applications. Context, as used herein, is an identification. A patient context may include a patient name (first, last, and middle names), social security number, address, phone number, email address, driver's license number, date of birth, patient identification number, etc. The context may also include an accession number, examination date, study identifier, or context code, which may be specifically indicative of a study associated with the patient, such as a radiological study of the patient.

A method, apparatus, and computer program product are provided in accordance with an example embodiment in order to provide a tool to synchronize contexts across a plurality of participating applications. Further, embodiments may identify applications that are not synchronized and may alert a user as such. The severity of any out-of-sync case may also be determined based on various factors, such as the time being out-of-sync in a workflow cycle and an acknowledgement of an out-of-sync issue by a user. The participating applications may periodically poll the synchronization tool of example embodiments to determine the context of the participating applications in order to ensure synchronization or to identify an out-of-sync condition.

One specific implementation of multiple electronic files associated with a particular patient may include a radiological study of a patient. There may be a variety of electronic files relating to a specific radiological study for a particular patient. For example, one electronic file may be a health record of the patient including patient information and patient diagnoses. Another electronic file may be a radiology image file associated with the patient. A third electronic file may include a dictation file associated with a radiology read order of the study. Various other files relating to a patient and a radiology study of the patient may also be available. Each different electronic file may require a different application for interfacing or creating/editing/modifying the file. In practice, for example, a dictation file, a patient record, and a radiology image file should be opened in their respective applications, each file relating to the same patient. These applications become participating applications when collaborating for review and analysis of a patient. However, the applications associated with each of these files may be dissimilar in that they do not communicate with one another to identify the patient associated with the currently opened file. It may be up to a user, such as a healthcare professional, to ensure that each file running in each application is associated with the same patient. However, such reliance on a user may be problematic and may result in user error.

FIG. 1 illustrates a system for synchronizing context across multiple participating applications, providing an indication when applications are out of synchronization, enabling the participating applications to determine synchronization state, and displaying differing states of synchronization. It will be appreciated that the system as well as the illustrations in other figures are each provided as example embodiments and should not be construed to narrow the scope or spirit of the disclosure. In this regard, the scope of the disclosure encompasses many potential embodiments in addition to those illustrated and described herein. As such, while FIG. 1 illustrates one example of a configuration of a system, numerous other configurations may also be used to implement embodiments of the present invention.

As shown in FIG. 1, a system in accordance with an example embodiment of the present invention may include a client 140 which may provide a graphical user interface to a user at user's location, such as in a healthcare facility. The client 140 may be embodied as a user terminal such as a laptop computer, workstation, or other like computing device, where multiple participating applications may be executed or interfaced with in order to review various electronic files relating to the same entity or subject. According to the example embodiment described herein, users, such as physicians, staff, radiologist, and/or other individuals may use the client 140 to access the various participating applications. The users may use the client 140 to access, review, update, delete, or create information or electronic files used by the system as described further below.

The illustrated system of FIG. 1 may include a server 120 which may be embodied as a server bank, other computer, other computing device, or node configured to provide services as described herein with respect to the illustrated example embodiments. As such, for example, the server 120 may be a platform, such as a dedicated server (or server bank), or the server may be a backend server associated with one or more other functions or services. The participating applications may be executed at the client 140 or at the server 120 and viewed at the client 140, such as over a virtual private network (VPN) or the like.

The system of FIG. 1 may further include a network 110 which may be embodied as a local area network (LAN), the Internet, a wide area network (WAN), or any other form of a network, or in any combination thereof, including proprietary private and semi-private networks and public networks. The network 110 may include a wired network, wireless network (e.g., a cellular network, wireless local area network, wireless wide area network, some combination thereof, or the like), or a combination thereof, and in some example embodiments may comprise at least a portion of the Internet. The network 110 may facilitate communication between the client 140, the server 120, and database 130. Further, while the illustrated embodiments depict the server 120, client 140, and database 130 as separate entities, the illustrated entities may be, in part or in all, remotely located communicating via the network, co-located communicating via a network or wired connection, or any combination thereof. In some example embodiments, the client 140, server 120, and database 130, may be implemented as a distributed system or a cloud based entity that may be implemented within the network 110. In this regard, the client 140 and server 120 may include one or more servers, server clusters, one or more network nodes, a cloud computing infrastructure, or some combination thereof.

One or both of the client 140 and server 120 may be configured to be in communication with a database 130 over network 110. The database 130 may be embodied as or comprise one or more computing devices configured to store data and provide data upon request to components of the system. In some example embodiments provided herein, the database 130 may be operative to store information associated with the patients. For example, the database 130 may be used to systematically manage any information such as patient records, patient radiology studies, and patient laboratory reports, among others. The database 130 may be configured to receive data from any apparatus of the system and/or external from the system, such as from a third party system. The database 130 may operate independently from server 120 and/or under different ownership than that of the client 140, but it will be appreciated that in some embodiments, the database 130 may indeed be operated separately but nonetheless by the same entity in control of the server 120.

Although FIG. 1 depicts one database 130, in some embodiments, any number of databases 130 may be present. In some example embodiments provided herein, database 130 may be configured to operate under control of a database management system (DBMS). In some examples, database 130 may be configured to provide data to various servers and/or subsystems of the system.

FIG. 2 illustrates an example of a client 140 (such as client 140 of FIG. 1) according to an example embodiment of the present invention. It should be noted that the components, devices, and elements illustrated in and described with respect to FIG. 2 below may not be required and thus some may be omitted in certain embodiments. Additionally, some embodiments may include further or different components, devices, or elements beyond those illustrated and described with respect to FIG. 2.

According to the embodiment of FIG. 2, the client 140 may include processing circuitry 210 configured to perform actions in accordance with one or more example embodiment disclosed herein. In this regard, the processing circuitry 210 may be configured to perform and/or control performance of one or more functionalities of the client 140 in accordance with various embodiments. The processing circuitry 210 may be configured to perform data processing, application execution, and/or other processing and management services according to one or more example embodiments. In some embodiments, the client 140 may be embodied or comprise a computing device, e.g., an integrated circuit or other circuitry. The circuitry may constitute means for performing one or more operations for providing functionalities described herein.

According to some embodiments, the processing circuitry may include a processor 212 and may further include a memory 214. The processing circuitry 210 may be in communication with or otherwise control a user interface 216, and/or a communication interface 218. As such, the processing circuitry 210 may be embodied as a circuit chip (e.g., an integrated circuit) configured (e.g., with hardware, software, or a combination of hardware and software) to perform the operations described herein.

The processor 212 may be embodied in a number of different ways. According to some embodiments, the processor 212 may include one or more microprocessor, controller, coprocessor, or other computing or processing devices including integrated circuits. Although the illustrated embodiment includes only a single processor 212, examples may be embodied by a plurality of components cooperating to perform the functions of the illustrated processor, such as a plurality of processors embodied on a single device or across multiple devices operating collectively to function as client 140. The processor 212 may be configured to execute instructions stored in the memory 214 or otherwise accessible to the processor 212. Thus, the processor 212, either configured as hardware or a combination of hardware and software, may represent an entity capable of performing operations in accordance with that which is described herein. When the processor 212 is embodied as circuitry, the processor 212 may be specifically configured for conducting these operations. According to another example, the processor 212 may be embodied as an executor of software instructions which may specifically configure the processor 212 to perform one or more operations described herein.

The memory 214 may include one or more non-transitory memory devices such as, for example, volatile and/or non-volatile memory that may be either fixed or removable. The memory 214 may include a non-transitory computer-readable storage medium. While the illustrated embodiment of the memory 214 is depicted as a single memory, it is appreciated that the memory 214 may include a plurality of memory devices collocated or remotely located from one another collectively configured to function as the memory 214 of the client 140. The memory 214 may be configured to store information, data, applications, instructions and/or the like for enabling client 140 to carry out various functions in accordance with one or more example embodiments. According to some embodiments, the memory 214 may be configured to buffer input data for processing by the processor 212, or to store instructions for execution by the processor 212. In some cases, the memory 214 may be in communication with one or more of the processor 212, user interface 216, and/or communication interface 218, for passing information among components of the client 140 and/or the system 100 of FIG. 1.

The user interface 216 may be in communication with the processing circuitry 210 to receive an indication of a user input at the user interface 216 and/or to provide an audible, visual, mechanical, or other output to the user. As such, the user interface 216 may include, for example, a keyboard, a mouse, a joystick, a display, a touch screen display, a microphone, a speaker, and/or other input/output mechanisms. As such, the user interface 216 may, in some example embodiments, provide means for user control of managing or processing data access operations and/or the like. For example, in instances client 140 is implemented in system 100 for radiological study analysis, a user may provide radiology read information, diagnosis, observations, and dictation information via the user interface 216, and may receive warnings or alerts via graphical user interface and/or an audible alert from the speaker.

While the apparatus of FIG. 2 is described herein as the client 140 of system 100, according to some embodiments, the server 120 may be embodied by a substantially similar apparatus. In such embodiments, aspects of the user interface 216 may be limited or the user interface 216 may not be present. Accordingly, regardless of implementation, the user interface 216 may provide input and output means in accordance with one or more example embodiments such as synchronizing contexts across a plurality of participating applications.

The communications interface 218 may include any mechanism for enabling communication with other devices and/or networks. The communications interface 218 may be, for example, hardware, software, or a combination thereof, that may receive and/or transmit data to and from a network or other device operating in communication with processing circuitry 210. The communication interface 218 may be configured to enable communication among the client 140, the server 120, and/or the database 130 via network 110. Accordingly, the communication interface 218 may, for example, include supporting hardware and/or software for enabling wireless and/or wired communications via cable, digital subscriber line (DSL), universal serial bus (USB), Ethernet, or other methods.

Having now described system 100 configured to implement and/or support implementation of various example embodiments, features of several example embodiments will now be described. It will be appreciated that the following features are non-limiting examples of features provided by some example embodiments. Further, it will be appreciated that embodiments are contemplated within the scope of disclosure that implement various subsets or combinations of the features further described herein. Accordingly, it will be appreciated that some example embodiments may omit one or more of the following features and/or implement variations of one or more of the following features.

Embodiments of the present invention may provide a system or tool for synchronizing contexts across a plurality of participating applications, providing an indication of out-of-sync applications from among the participating applications, present varying states of synchronization between the participating applications, and enable the participating applications to determine the contexts of the various other participating applications. A system of an example embodiment may include a client 140 executing (via processing circuitry 210) or accessing (via communication interface 218) a plurality of applications. These applications may be interrelated as applications configured to be used in collaboration for the review, observation, analysis, and diagnosis of the condition of a patient. According to an example embodiment of a radiology information system, the applications may include, among other applications, a radiology picture archiving and communication system (PACS) application, a dictation application (e.g., text-to-speech transcribing application), an electronic medical record (EMR) viewer/editor, etc. These applications may be the collaborating applications that may be joined to become participating applications.

According to embodiments described herein, the system may include a synchronization tool or application which is configured to join together the operation of a plurality of applications in collaboration as participating applications. The synchronization tool may be pre-configured with the plurality of applications that are anticipated or required to be participating applications for the synchronization tool. The plurality of applications may include one or more "required" applications while additional applications may be optional. In operation, the synchronization tool may determine which applications are to be used and join the applications using the synchronization tool to enable various features described herein.

Applications that are used in collaboration with other applications in a system such as a radiology information system may provide a "join" message in response to execution or initiation of the application. The "join" message may be provided to the synchronization tool indicating that the application is requesting to join a collaboration to become a participating application. Each of the plurality of applications may provide this "join" request such that upon execution or initiation of the applications, they are joined in collaboration as participating applications through the synchronization tool. Optionally, the synchronization tool may launch or execute the applications that are to become participating applications. Once the plurality of applications are running and have joined the collaboration at the synchronization tool, they become the plurality of participating applications. Participating applications may also be configured to send messages relating to contexts, as described below, requests for the current synchronization state, and a "leave" message when the participating application is being closed or ceasing to participate in the collaboration of participating applications. Participating applications may optionally be configured to send "pause" and "resume" messages as will be detailed further below.

According to example embodiments described herein, none of the participating applications are deemed a managing application or a primary application. Each participating application may initiate a context change event and may effectively initiate a context synchronization event. Accordingly, one of the participating applications may open a new electronic file, such as a PACS application opening a radiology study file. The electronic file opened by the participating application may include a context, which may include a patient context code, an accession number, patient identifiers, facility code, or the like as described above. The context of the electronic file uniquely identifies the subject of the electronic file. In an example embodiment of a radiology information system, the context may identify the patient, the radiology study, and the facility from which the study came. This application opening a new electronic file having a new context may be treated as a context change starter for the synchronization tool. A context change starter may be signified by: 1) the context of the file executed in the application has changed from a previous context or from an empty context; 2) the application is the first application to change context since a prior synchronization state or empty state in all participating applications; 3) the new context is different from current contexts in the other participating applications. An empty context exists when an application is running, but no electronic file is opened within the application, such that no context is associated with the application.

Participating applications may provide and receive messages in a variety of different formats such that the synchronization tool of example embodiments may provide an interface module enabling a wide range of integration interfaces, such as extensible markup language (XML), command line, universal resource locator (URL), or the like. This interface module may enable applications with dissimilar communication protocols to properly communicate with the synchronization tool.

According to some embodiments, patient contexts may be formatted or encoded differently across disparate applications. The synchronization tool described herein may further include a data mapping module that is configured to map contexts from a first application to contexts from a second, different application, regardless of the format of the context. For example, an accession number may be used by a first application to identify a context of an electronic file opened by that application. A second application may use a prefix for the same accession number. The context identifiers used by these two applications may be mapped to one another using the data mapping module in order to be able to accurately compare the contexts in determining if they reference the same patient and study. The synchronization tool may be configured to identify specific features of a context in order to match one context to another. The specific features of context to be matched may be user configurable based on the specific environment of use, such as a healthcare facility that may depend upon accession number and patient identification.

This "context change starter" initiated by the first application opening an electronic file having a new context begins the synchronization process or synchronization cycle of the synchronization tool. The application that opens a new file having a new context sends a context change message to the synchronization tool. The synchronization tool, in response to the context change starter being received, may update the context associated with the respective application from which the context change starter was received. This begins the context synchronization cycle. The synchronization tool, in response to initiating the context synchronization cycle, anticipates context changes from the other participating applications, and provides synchronization states, alerts, and warnings based on what, if any, context changes are received from the remaining participating applications.

The message sent from the participating applications indicative of a context change may optionally include a context synchronization state. The context synchronization states may include an "In Progress" state indicating that some applications already changed contexts but others have not changed, an "Out-of-Sync" state indicating that all participating applications change contexts but some of them do not match, an "Empty Context" state when there is no file opened in every application, a "Previous Out-of-Sync" state notifying the synchronization tool of a previous Out-of-Sync condition, and a "Synchronized" state affirming that the context of the open file is aligned with the other participating applications.

FIG. 3 depicts an example embodiment of the message flow between applications and the synchronization tool of the present invention. The participating applications are depicted at 300. These applications may be running at the client 140, such as using processing circuitry 210. Upon an application opening a first or a new electronic file having a first context, the context message is sent to the message receiver 310 as message 305. The context synchronization processor 320 (which may be embodied by processing circuitry 210), may determine if any other participating applications are running with electronic files matching the context. If no other participating applications are running with electronic files matching the context, the message is treated as a context change starter to initiate the synchronization cycle.

The context state of each participating application may be sent to the message receiver 310 in response to a new electronic file being opened having a new context at each respective participating application. Optionally, the context synchronization processor 320 may request context state from each of the participating applications. The current context of each participating application, whether proactively provided by the application or provided in response to a request, may be maintained at the context synchronization processor 320. The synchronization state may be determined based on the contexts reported by each of the participating applications and the context state provided by the participating applications, if available.

FIG. 4 illustrates example embodiments of a synchronization cycle. The examples illustrate a system having three participating applications: a radiology information software (RIS) application; a PACS application; and a reporting application. The illustrated applications are generic applications illustrated merely for example and are not intended to be limiting. As will be appreciated, any relevant application may be used depending upon the implementation of the synchronization tool. As shown in Example 1, at time 0:00.0, each of the applications has an empty context represented by the dash: "-". This may be the case when the applications are initially opened and joined at the synchronization tool (e.g., by context synchronization processor 320 of FIG. 3). The RIS application opens a new file having a context of "A" at time 0:00.5. Since the context reported by the RIS application is new and different from the other participating applications, the context synchronization processor 320 considers the RIS application the context change starter. At time 0:00.5, the applications are at "In Progress" state since the PACS and Reporting applications have not had the same context as the RIS application. At time 0:01.0, the PACS application has opened a file with corresponding context A and reported this context change in a message to the synchronization tool as shown at 305 of FIG. 3. The three applications remain "In Progress" since the Reporting application has not yet opened a file corresponding to context A. At time 0:02.0, the Reporting application sends a message indicating that the Reporting application has opened a file corresponding to context A such that the three participating applications are operating on the same context and are therefore synchronized. The time provided in the examples discussed herein is intended merely for reference and is not indicative of the actual time required to perform any of the operations discussed herein. Further, the time of 0:00.0 is not intended to be the beginning of a timer, as will be discussed further below, but is merely a reference time from which the examples begin.

Referring back to FIG. 3, the context synchronization processor 320 may provide an output to output indicator 330, which may provide an indication to a user. The output from the context synchronization processor may be out-of-sync or synchronized, but may have various other synchronization states as will be detailed further below. The synchronization state may be stored at context synchronization tracking server 350 to provide an indication with the electronic files being viewed as to their synchronization. For example, a synchronized state may provide confirmation that the analysis of the electronic files reviewed in the collaborating applications were properly reviewed. However, an out-of-sync state may provide an indication that one or more applications was not synchronized during the review of the electronic files in the collaborating applications, suggesting a review of the analysis may be merited.

As shown in FIG. 4, Example 2 begins with the RIS application, PACS application, and Reporting application synchronized at time 0:00.0 with each participating application synchronized to context A. At time 0:01.0, the PACS application sends a message to the synchronization tool indicative of opening a file corresponding to a context B. This change of context signifies that the PACS application is a starter application starting the context change from A to B. At time 0:01.5, the RIS application has closed the file associated with context A, but no file is presently opened and no context is reported. The context synchronization state at this point is "In Progress" as the synchronization tool acknowledges that insufficient time has passed to allow all participating applications to be synchronized. The amount of time allowed by the synchronization tool for synchronization to occur may be based on the processing speed of the client 140 and the number of participating applications, for example. This amount of time may be user configured, or may be learned by the context synchronization processor 320. The Reporting application remains on context A at time 0:01.5, such that the reporting application is out-of-sync. However, as noted, an Out-of-Sync state may not yet be communicated as instantaneous context synchronization is not anticipated by the synchronization tool. At time 0:02.0, the reporting application has closed the file associated with context A. At time 0:02.5, the RIS application has opened the file and reported the associated context of B, while at time 0:03.0, the Reporting application has opened the file and reported the associated context of B. Thus, at time 0:03.0, the participating applications are again synchronized. Once all participating applications have reported a context aligned with the context starter, the context synchronization state may be output to 330 as Synchronized.

As illustrated in Examples 1 and 2, participating applications may be out-of-sync for periods of time, though that out-of-sync period may be of little or no concern depending on how long the out-of-sync period is, and the contexts of the participating applications during that period. As evident from the Examples of FIG. 4, it may be more appropriate to classify context synchronization in varying states rather than simply synchronized and out-of-sync. According to embodiments described herein, numerous states relating to context synchronization may be established. States may include: No Context, Local Context Only, In Progress, In Progress but Timed Out; Synchronized, Context Changed, and Out-of-Sync.

The context state of "No Context" is illustrated in Example 1 in which the RIS, PACS, and Reporting applications each lack a context. This may be the case when an application is running, but no file is opened. This may also be the case when a file is initially opened, but a context is not yet established, such as by the data mapping module of example embodiments. The data mapping module may be embodied, for example, in context synchronization processor 320. The synchronization state of "Local Context Only" may be determined in an instance in which the context for at least one application is known, such as for the PACS application; however, the contexts for the other participating applications may not be known. This state may be similar to an Out-of-Sync state indicating a potential need for review, but does not definitively state or assert that the applications are out-of-sync.

In order to distinguish between applications that are synchronized, out-of-sync, and in various stages of progress, a time component is incorporated into the determination of synchronization state. The synchronization states of "In Progress" and "In Progress but Timed Out" may identify states that are before synchronization, where synchronization has not yet been established. For example, referring back to Example 1 of FIG. 4, at time 0:00.0, the synchronization state may be "No Context" as none of the applications have an associated context. At 0:00.5, the RIS application has initiated a context change starter, and the context synchronization state may be "Local Context Only." This context change starter may initiate a timer or establish a baseline time over which the context change should occur. The synchronization state at time 0:01.0 may optionally be "In Process" as the participating applications are not synchronized; however, as the RIS application just started a file associated with context A, but immediate synchronization is not expected. At time 0:01.0, an amount of time has elapsed and PACS application has opened a file associated with context A. While Reporting application has not yet opened a file associated with a context. As the amount of time elapsing is relatively low, a determination may be made that the synchronization is still In Process. At 0:02.0, the Reporting application has opened a file associated with context A, and the participating applications are synchronized.

The synchronization state may be provided to a user to inform them of the context states of the participating applications. For example, the output indicator 330 may receive an indication that the synchronization is "In Process" at time 0:01.0 of Example 1, and that output indicator may provide a visual indication to a user, such as through user interface 216. This may alert the user that not all participating applications are synchronized yet. Further, this "In Progress" indication may indicate the number of participating applications synchronized, together with their identities, and the elapsed time since the context synchronization was started. This information may preclude a user from beginning work on the participating applications before they each present the files of the same context. The "In Progress" synchronizations state may be used for a predetermined amount of time after the context synchronization start. This predetermined amount of time may be based on a variety of factors including the number of participating applications, the speed of the processing circuitry 210, the complexity of the files being opened, etc. Further, this predetermined time may be user adjustable. This synchronization state of "In Progress" may be established and/or presented in response to the amount of time elapsing since the context synchronization start satisfying a first criterion, such as that the time is greater than half of a second. The "In Progress" condition may be considered a type of out-of-sync condition, but within the allotted amount of time for an out-of-sync condition to exist.

Another context synchronization state may include "In Progress but Timed Out." This context synchronization state may exist after a period of time in which the synchronization state was "In Progress," but synchronization was not achieved before a predetermined time. Such a synchronization state may indicate that the context synchronization was started, but failed to complete within a predefined period of time from the start. This predefined period of time may be, for example, several seconds. Referring again to Example 1 of FIG. 4, if the contexts of the RIS, PACS, and Reporting applications remained at the contexts illustrated at time 0:01.0 for five seconds, for example, the synchronization process may time out and an alert may be provided to a user, such as via Output Indicator 330 through Warning Dialog 360, that context synchronization was "In Progress, but Timed Out." Such a context synchronization state may optionally be accompanied by an audible alert to ensure the user is aware of the lack of alignment between contexts of the participating applications.

The context synchronization state may indicate "Out-of-Sync" after a predetermined amount of time. For example, after the synchronization state of In Progress, but Timed Out state, the context synchronization may transition to Out-of-Sync. This Out-of-Sync state may be indicative that contexts are not aligned between the participating applications, and it is not anticipated that the contexts will align. This may occur, for example, after a predetermined period of time after the context synchronization start. The Context Synchronization Processor 320 may provide an indication to the Output Indicator 330 and be presented to a user at Warning Dialog 360.

Another manner in which an Out-of-Sync context state can be achieved is illustrated in Example 3 of FIG. 5. As shown, the participating applications are synchronized at time 0:00.0, each with a context A. At time 0:01.0, the PACS application opens a new file with a context of "B". At 0:01.5, the RIS application closes the file associated with context A, but Reporting application still has open a file associated with context A. At time 0:02.0, the RIS application closes the file.

At time 0:02.5, the RIS application opens the file associated with context B. At time 0:03.0, the reporting application opens a file associated with context C. At time 0:03.0, the context synchronization status may be Out-of-Sync since a starter was found as the PACS application, and each participating application changed files to a new context. However, the Reporting application changed the file to a different context than the RIS or PACS application. This suggests that the Out-of-Sync is not due to delay, but instead due to an improper context.

Example 4 illustrates another example of how an Out-of-Sync context state may be achieved. At 0:00:0, the participating applications are synchronized with context A. Similar to Example 3, PACS becomes the starter application starting the context synchronization cycle at time 0:01.0. The RIS application closes the file related to context A at 0:02.0, while the Reporting application closes the file related to context A at 0:03.0. Before the RIS application and the Reporting application open another file with another context, the PACS application closes the file associated with context B and opens a file associated with context C at 0:04.0. The RIS application opens the file associated with context B at 0:05.0, but then closes that and opens the file associated with context C at 0:06.0. At 0:07.0, the Reporting application opens the file associated with context B. An Out-of-Sync context state may be established due to the delay between the PACS application opening a file associated with context C at 0:04.0, while the Reporting application only opens a file associated with context B at 0:07.0. This delay, together with the Reporting application remaining out-of-sync with the RIS application and the PACS application may cause an Out-of-Sync synchronization state. The Out-of-Sync state may be caused by the Reporting application failing to achieve a context of C within three seconds of the second context change initiated by the PACS application. This Out-of-Sync condition may provide a warning via Output Indicator and Content Sync viewer 340 to alert a user as to the out-of-sync condition.

As shown, various stages of context synchronization may occur during the synchronization cycle, and these states may be communicated to a user through warning dialog 360 of FIG. 3. Further, these synchronization states may be recorded and saved together with an analysis associated with the context(s) opened in the applications. The synchronization states may be saved together with the analysis whether they are temporary (such as "In Progress") or persistent (such as "Synchronized"). If there is delay between the opening of a file associated with a first context in a first application, and the opening of a file associated with the first context in a second application, it may be desirable for a user to understand how long the "In Progress" context synchronization state existed. A short duration may be of little or no concern, while a longer duration may indicate that there is a possibility that two different contexts were viewed during the analysis, at least for a period of time.

While the above-described examples illustrate the use of a maximum amount of time allowed to elapse before declaring an out-of-sync condition, the synchronization tool may provide a first amount of time given a first set of conditions before declaring an out-of-sync condition, while a second amount of time may be given for a second set of conditions. According to an example embodiment, once a context change starter is detected, a delay of one second may be afforded the participating applications in which to begin a context change. The participating applications may provide an indication such as "In Progress" to the context synchronization tool indicating that the context is being changed. This enables the context synchronization tool to await a new context from the respective application while there is no concern that an incorrect context remains presented on that application. If the participating applications do not report an "In Progress" state or a new context within a maximum amount of time, such as three seconds, an out-of-sync condition may be established. The out-of-sync condition achieved through reaching the maximum delay may be removed in response to a synchronized condition being reached. However, the synchronization tool may provide a warning to the user that requires acknowledgement of the condition that did exist. This ensures that the user did not ignore the out-of-sync condition. Whether or not the user acknowledges the condition may affect the determined severity of the condition as described further below.

The synchronization state associated with any context may be recorded and associated with the analysis that is performed at the client 140. For example, referring to Example 2 of FIG. 4, the analysis may indicate that a context change occurred including a delay of two seconds between the context change start (at 0:01.0) to synchronization (at 0:03.0). While this delay may be within the allowed time for a context change to occur, the delay may be included in the analysis to confirm minimal synchronization delay. The severity of this out-of-sync state may be considered minimal or low. Similarly, referring to Example 4 of FIG. 5, the analysis of the study of context C may include an indication that an out-of-sync condition was established during the context synchronization. The duration of this condition and whether or not it was acknowledged by the user may determine the associated severity. Further, the number of applications out-of-sync may contribute to the severity. Severity may be determined based on a score. A number of mismatched applications may provide a component of the score, while a second component of the score may be the duration of an out-of-sync condition, and a third component may include whether or not the out-of-sync condition was acknowledged.

A severity score may be calculated as follows:

| # of Mismatched Items | Score |
|---|---|
| 1 | 1 |
| 2 | 2 |
| 3 or more | 3 |

| Out of Sync Duration | Score |
|---|---|
| 0-10 seconds | 1 |
| 10+ seconds | 2 |

| Out-of-Sync | Score |
|---|---|
| Acknowledged | 1 |
| Not Acknowledged | 3 |

According to the tables above, two mismatched application contexts (2) out of sync for five seconds (1) without an acknowledgement (3) equates to a severity score of 6. An example in which there are three mismatched application contexts (3) for 11 seconds (2) without an acknowledgement (3) equates to the highest severity score of 8. The higher the severity score, the more likely an error can occur in the analysis of the contexts within the participating applications. This severity score may be included in the analysis of the contexts in order to provide a reviewer with an understanding of the possibility of issues with the analysis.

According to example embodiments provided herein, the synchronization tool may also be configured to enable participating applications to request and receive context states. Some participating applications may check synchronization periodically or at certain points through their function. These applications may send a request, such as at 380 of FIG. 3, to determine a current synchronization state 370 from the context synchronization processor 320. This information may be recorded by the requesting application, such as in the file associated with the current context. This information regarding synchronization state may be maintained to create an audit trail of synchronization states throughout the use of a particular participating application.

FIG. 6 illustrates a flowchart of the operations of a method of operation of a synchronization tool according to example embodiments of the present invention. At operation 505, an indication of two or more participating applications is received. This may be, for example, received at the context synchronization processor 320 in the form of "join" messages from the participating applications. A first patient context associated with a first file may be received by the context synchronization processor 320 in response to a first application of the participating applications accessing the file. The file may be stored, for example, in a radiology information database, such as database 130, at 510. A determination may be made by the context synchronization processor 320 as to whether the first patient context is different from patient contexts associated with other applications of the two or more other participating applications at 515. In response to determining that the first patient context is different from the patient contexts associated with the other applications, a timer may be initiated at 520. A determination may be made by the context synchronization processor regarding whether the patient contexts associated with the other applications have changed to become the first patient context at 525. A first notification may be provided by the context synchronization processor 320 through output indicator 330 in response to the patient context associated with at least one of the other applications not matching the first patient context and the timer satisfying a first criterion at 530. At 535, a second notification may be provided in response to the patient context associated with at least one of the other applications not matching the first patient context and the timer satisfying a second criterion.

As described above, FIG. 6 illustrates a flowcharts of a system, method, and computer program product according to example embodiments of the invention. It will be understood that each block of the flowcharts, and combinations of blocks in the flowcharts, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may be stored by one or more memories 214 of a client 140 and executed by processor 212 in the client. In some embodiments, the computer program instructions comprising the computer program product(s) which embody the procedures described above may be stored by memory devices of a plurality of computing devices or clients.

As will be appreciated, any such computer program product may be loaded onto a computer or other programmable apparatus to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product comprises an article of manufacture which implements the function specified in the flowchart block(s). The computer program instructions of one or more computer program products may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks or steps of the flowcharts support combinations of means for performing the specified functions and combinations of steps for performing the specified functions. It will also be understood that one or more blocks of the flowcharts, and combinations of blocks in the flowcharts, may be implemented by special purpose hardware-based computer systems which perform the specified functions or steps, or combinations of special purpose hardware and computer program product(s).

The above described functions may be carried out in many ways. For example, any suitable means for carrying out each of the functions described above may be employed to carry out embodiments of the invention. In one embodiment, a suitably configured processor 212 may provide all or a portion of the elements of the invention. In another embodiment, all or a portion of the elements of the invention may be configured by and operate under control of a computer program product. The computer program product for performing the methods of embodiments of the invention includes a computer-readable storage medium, such as the non-volatile storage medium, and computer-readable program code portions, such as a series of computer instructions, embodied in the computer-readable storage medium.

Many modifications and other embodiments of the inventions set forth herein will come to mind to one skilled in the art to which these inventions pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A radiology information system comprising a processor, at least one non-transitory memory having program code portions stored thereon, and a radiology information database having radiology images stored therein, the program code portions configured, upon execution, to:
   receive an indication of two or more participating applications;
   receive a first patient context associated with a first file in response to a first application of the two or more applications accessing the first file associated with a first patient stored in the radiology information database;
   determine if the first patient context is different from patient contexts associated with other applications of the two or more participating applications;
   initiate a timer in response to determining that the first patient context is different from the patient contexts associated with the other applications;
   determine if the patient contexts associated with the other applications have changed to become the first patient context;
   provide a first notification in response to the patient context associated with at least one of the other applications not matching the first patient context and the timer satisfying a first criterion; and
   provide a second notification in response to the patient context associated with at least one of the other applications not matching the first patient context and the timer satisfying a second criterion.

2. The system of claim 1, further comprising program code portions configured to:
   provide a third notification in response to the patient contexts associated with the other applications matching the first patient context.

3. The system of claim 1, further comprising program code portions configured to:
   map the patient contexts associated with the two or more participating applications to a common patient context format.

4. The system of claim 1, wherein the first notification comprises an in-progress notification indicating a number of the other applications associated with patient contexts not matching the first patient context.

5. The system of claim 4, wherein the program code portions configured to provide a second notification in response to the patient context associated with at least one of the other applications not matching the first patient context comprises program code portions configured to provide an indication of a number of applications for which a patient context does not match the first patient context.

6. The system of claim 5, further comprising program code portions configured to:
   determine a severity level based on a number of other applications for which a patient context does not match the first patient context and the timer satisfying the first criterion and a number of other applications for which a patient context does not match the first patient context and the timer satisfying the second criterion; and
   append information associated with one of the first notification or the second notification and the determined severity level to a study associated with the first patient.

7. An apparatus comprising a processor and at least one non-transitory memory having computer-executable program code instructions stored therein, the processor configured, in response to execution of the computer-executable program code instructions, to cause the apparatus to:
   receive an indication of two or more participating applications;
   receive a first patient context associated with a first file in response to a first application of the two or more applications accessing a study associated with a first patient;
   determine if the first patient context is different from patient contexts associated with other applications of the two or more participating applications;
   initiate a timer in response to determining that the first patient context is different from the patient contexts associated with the other applications;
   determine if the patient contexts associated with the other applications have changed to become the first patient context;
   provide a first notification in response to the patient context associated with at least one of the other applications not matching the first patient context and the timer satisfying a first criterion;
   provide a second notification in response to the patient context associated with at least one of the other applications not matching the first patient context and the timer satisfying a second criterion; and
   append information associated with one of the first notification or the second notification to the study associated with the first patient.

8. The apparatus of claim 7, wherein the file comprises a radiology study, and wherein at least one of the two or more applications comprises a radiology image viewing application.

9. The apparatus of claim 7, wherein the apparatus is further configured to map the patient contexts associated with the two or more participating applications to a common patient context format.

10. The apparatus of claim 7, wherein the first notification comprises an in-progress notification indicating a number of the other applications associated with patient contexts not matching the first patient context.

11. The apparatus of claim 10, wherein causing the apparatus to provide a second notification in response to the patient contexts associated with the other applications not matching the first patient context comprises causing the apparatus to provide an indication of a number of applications for which a patient context does not match the first patient context.

12. The apparatus of claim 11, wherein the apparatus is further configured to:
   determine a severity level based on a number of other applications for which a patient context does not match the first patient context and the timer satisfying the first criterion and a number of other applications for which a patient context does not match the first patient context and the timer satisfying the second criterion; and
   include the severity level in the information appended to a study associated with the first patient.

13. The apparatus of claim 12, wherein the apparatus is further configured to:
   receive an acknowledgement of the first notification or the second notification, wherein causing the apparatus to determine the severity level is further based on whether an acknowledgment is received for the first notification or the second notification.

14. A method comprising:
   receiving an indication of two or more participating applications;

receiving a first patient context associated with a first file in response to a first application of the two or more applications accessing a file associated with a first patient;

determining if the first patient context is different from patient contexts associated with other applications of the two or more participating applications;

initiating a timer in response to determining that the first patient context is different from the patient contexts associated with the other applications;

determining if the patient contexts associated with the other applications have changed to become the first patient context;

providing a first notification in response to the patient context associated with at least one of the other applications not matching the first patient context and the timer satisfying a first criterion;

providing a second notification in response to the patient context associated with at least one of the other applications not matching the first patient context and the timer satisfying a second criterion; and appending information associated with one of the first notification or the second notification to the study associated with the first patient.

15. The method of claim 14, wherein the study comprises a radiology study, and wherein at least one of the two or more applications comprises a radiology image viewing application.

16. The method of claim 14, further comprising mapping the patient contexts associated with the two or more participating applications to a common patient context format.

17. The method of claim 14, wherein the first notification comprises an in-progress notification indicating a number of the other applications associated with patient contexts not matching the first patient context.

18. The method of claim 17, wherein providing the second notification in response to the patient contexts associated with the other applications not matching the first patient context comprises providing an indication of a number of applications for which a patient context does not match the first patient context.

19. The method of claim 18, further comprising:
determining a severity level based on a number of the other applications for which a patient context does not match the first patient context and the timer satisfying the first criterion and a number of the other applications for which a patient context does not match the first patient context and the timer satisfying the second criterion; and including the severity level in the information appended to the study associated with the first patient.

20. The method of claim 19, further comprising:
receiving an acknowledgement of the first notification or the second notification, wherein determining a severity level is further based on whether an acknowledgment is received for the first notification or the second notification.

* * * * *